United States Patent [19]
Porte et al.

[11] Patent Number: 5,073,342
[45] Date of Patent: Dec. 17, 1991

[54] RECIPROCATING TRANSFER MECHANISM

[75] Inventors: Johannes J. Porte, Webster; Raymond F. Jakubowicz, Rush, both of N.Y.

[73] Assignee: Eastman Kodak Company, Rochester, N.Y.

[21] Appl. No.: 293,712

[22] Filed: Jan. 5, 1989

[51] Int. Cl.$^5$ ............................................. G01N 35/00
[52] U.S. Cl. ....................................... 422/64; 422/63; 436/46; 414/223; 414/749; 198/468.6; 198/468.11
[58] Field of Search ....................... 422/63, 64, 65, 67; 436/46; 414/19, 223, 749; 198/468.6, 468.11, 410

[56] References Cited

U.S. PATENT DOCUMENTS

| | | |
|---|---|---|
| 4,224,032 | 9/1980 | Glover et al. |
| 4,269,803 | 5/1981 | Jessop. |
| 4,302,420 | 11/1981 | Jakubowicz et al. |
| 4,568,519 | 2/1986 | Hamilton et al. |
| 4,584,275 | 4/1986 | Okano et al. |
| 4,629,056 | 12/1986 | Simelunas et al. ............... 198/410 |
| 4,855,109 | 8/1989 | Muraishi et al. ............... 422/65 |
| 4,867,631 | 9/1989 | Warenback et al. ............... 414/416 |

Primary Examiner—Robert J. Warden
Assistant Examiner—D. John Griffith, Jr.
Attorney, Agent, or Firm—Dana M. Schmidt

[57] ABSTRACT

There is disclosed a simplified transfer mechanism that minimmizes both the number of moving parts needed, and the shapes of those parts. An L-shaped pusher blade is mounted to move in and out of a first station such as at an incubator so as to be effective to move a test element from the first station to two or more subsequent stations.

10 Claims, 5 Drawing Sheets

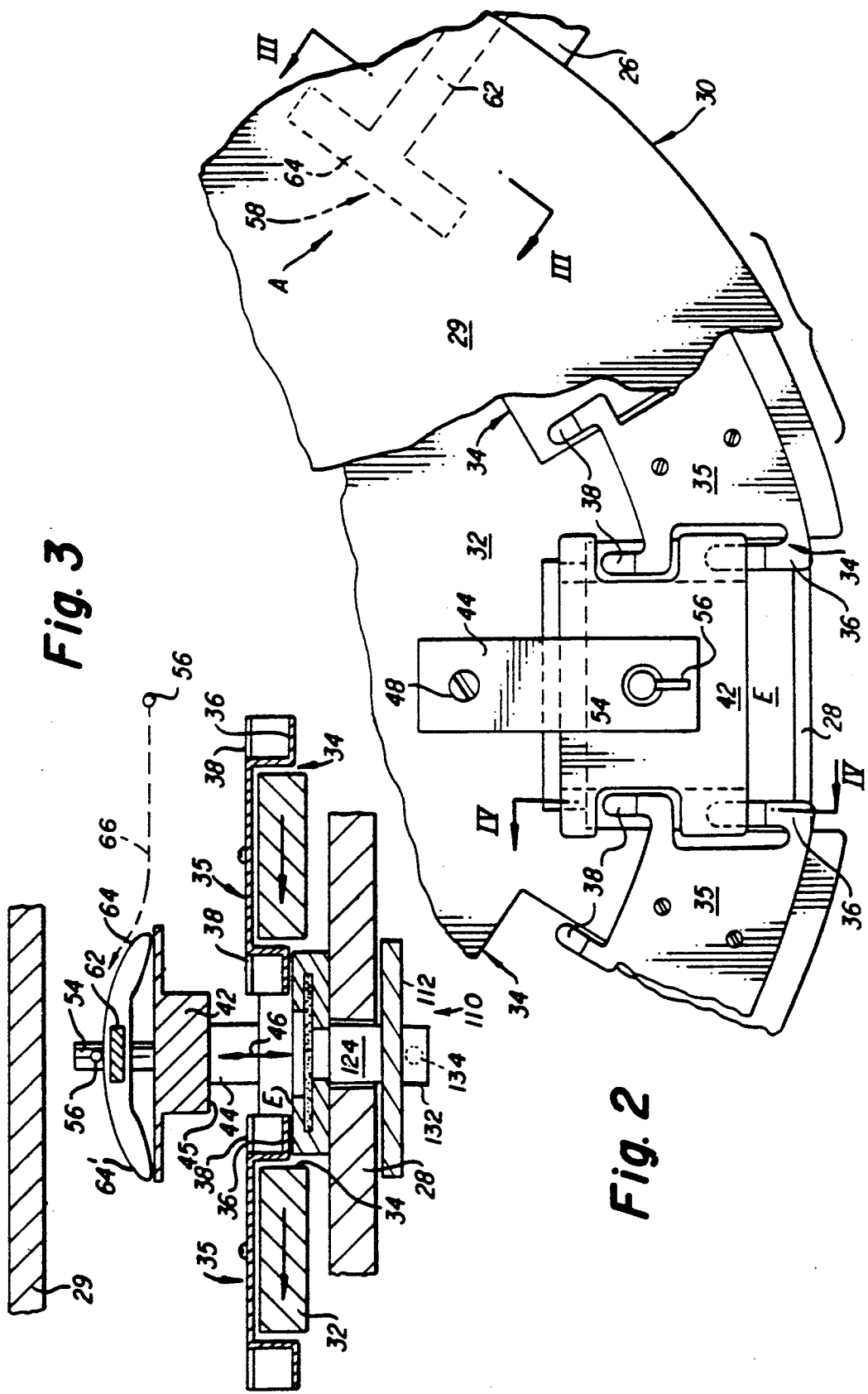

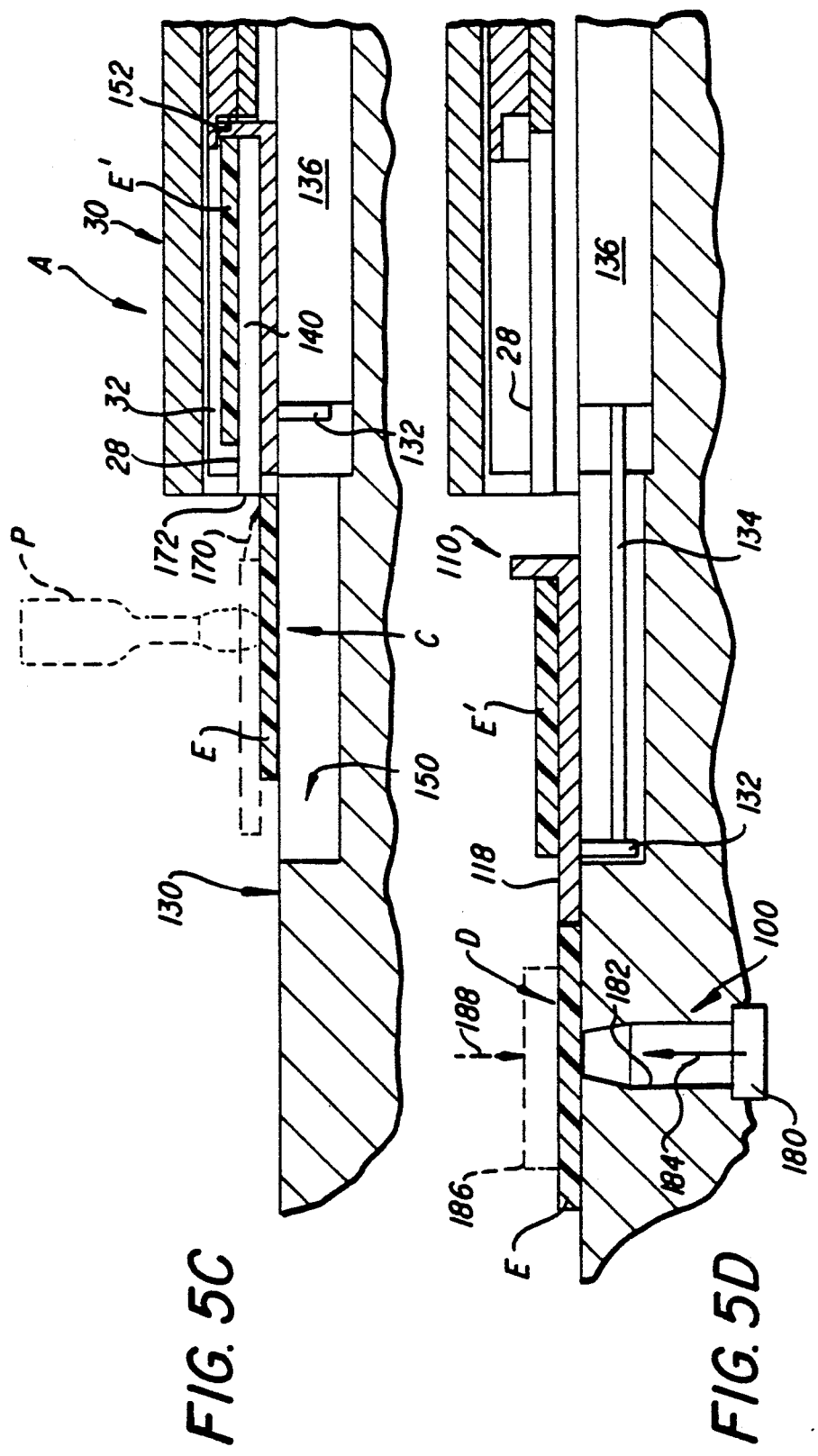

5,073,342

RECIPROCATING TRANSFER MECHANISM

FIELD OF THE INVENTION

The invention relates to a transfer mechanism useful in moving test elements to a plurality of locations, particularly in an analyzer.

BACKGROUND OF THE INVENTION

A pusher blade such as is used in a transfer mechanism of a blood analyzer normally has an edge or portion thereof that engages test elements to push them from location A to location B. As such, a single blade has limited capability for moving such an element. The result is that if the test element has to be moved to yet other locations, locations C and/or D, some other mechanism or moving agent besides that pusher blade, must be employed. Examples of such a construction are shown in U.S. Pat. No. 4,244,032, FIG. 5, and in U.S. Pat. No. 4,302,420. U.S. Pat. No. 4,269,803 teaches a shuttle block 52 used to carry a test element from its position at station 20, left there by pusher blade 31, through more than 2 stations. That is, shuttle 52 has two pivoted, engaging surfaces or fingers 60 at the front and rear of the shuttle that project through support 25. Using the rear finger, the shuttle is able to take a test element from a "first" position at station 20, FIG. 3a, to a "second" position at station 27, FIG. 3b. When shuttle 50 is reciprocated back, and then forward again, the other, forward finger then pushes that same test element to a "third" location which is the eject station adjacent bin 66, FIG. 3c.

Thus, the aforesaid shuttle 50 comprises a moving element able to move test elements to more than two locations. However, for every location beyond two, it requires an extra upwardly projecting pivoted finger. Such a construction renders the shuttle block considerably more complicated than a simple pusher blade, and thus more expensive to manufacture. Furthermore, it is a well-established principle that the more complicated a mechanism becomes, the more likely it is that something will go wrong with it.

Therefore, there has been a need prior to this invention, to provide a less expensive form of moving element which nevertheless will move a test element through three and even four stations or locations, without necessitating the use of some other moving part.

There is an additional need to provide apparatus that is useful in environments having less than the Earth's gravity. For example, space stations have a need for blood analyzers that can operate in zero gravity.

SUMMARY OF THE INVENTION

We have constructed a transfer mechanism that solves the problems noted above—it provides movement of a test element from a first station to a second and third station, and even a fourth station, without the complexities required by prior art constructions.

More specifically, there is provided, in one aspect of the invention, a transfer mechanism for moving a test element from a first location to other locations. The transfer mechanism comprises a first support surface providing the first location, a pusher blade under the first support surface, having a leading portion and a rear portion, means for moving the blade from a location in which it is directly under the first support surface to one in which it is no longer under the support surface, an upwardly extending finger integrally extending from the rear portion of the pusher blade, the first support surface having a slot to accommodate the finger, a pushing surface at the leading portion of the pusher blade, and a support surface on the blade between the leading and rear portion, constructed to receive and support a test element.

In accord with another aspect of the invention, there is provided a biological liquid analyzer comprising means for incubating a test element containing a patient liquid, the incubating means including a test element support surface at a first location, means for processing an incubated test element, and a transfer mechanism for moving a test element from the first location to the processing means. The analyzer is improved in that the transfer mechanism includes a pusher blade under the first support surface, having a leading portion and a rear portion, means for moving the blade from a location in which it is directly under the first support surface to one in which it is no longer under the support surface, an upwardly extending finger integrally extending from the rear portion of the pusher blade, the first support surface having a slot to accommodate the finger, a pushing surface at the leading portion of the pusher blade, and a support surface on the blade between the leading and rear portion, constructed to receive and support a test element.

In accord with yet another aspect of the invention, there is provided a method of moving a test element through more than two separate locations using a single moving element, the first of the locations being located on a first stationary support surface and the moving element being movably located under the support surface with means to guide it out from underneath the support surface with a clearance less than the thickness of a test element. The method comprises the steps of a) disposing a test element into the first location on the support surface; b) positioning the moving element while underneath the support surface so that a rear portion of the moving element projects through the support surface into contact with a rear edge of a test element; c) moving the moving element out from underneath the support surface until the projecting portion pushes the contacted test element off the support surface into a second location on the moving element; and d) retracting the moving element underneath the support surface until the support surface pushes a test element carried by the moving element, off of it into a third location on a second support surface in front of the moving element.

Accordingly, it is an advantageous feature of the invention that a simplified pusher blade transfer mechanism is provided for an analyzer, that can transfer a test element between three and even four stations.

It is a related advantageous feature of the invention that such a transfer mechanism is capable of such results, and still be in the form of a simple integral L-shaped blade.

Another related advantageous feature of the invention is the reduction in cost achieved by such a device.

Other advantageous features will become apparent upon reference to the detailed description of the preferred embodiments, when read in light of the attached drawings.

BRIEF DESCRIPTION OF THE DRAWINGS

FIG. 2 is a fragmentary, enlarged plan view similar to that of FIG. 1, illustrating greater detail;

FIG. 3 is a fragmentary section view taken generally along the line III—III of FIG. 2;

FIGS. 5A-5D are fragmentary elevational views partly in section, taken generally through the plane of arrow 46 in FIG. 3, and illustrating a preferred practice of the invention.

DESCRIPTION OF THE PREFERRED EMBODIMENTS

Figure 1:
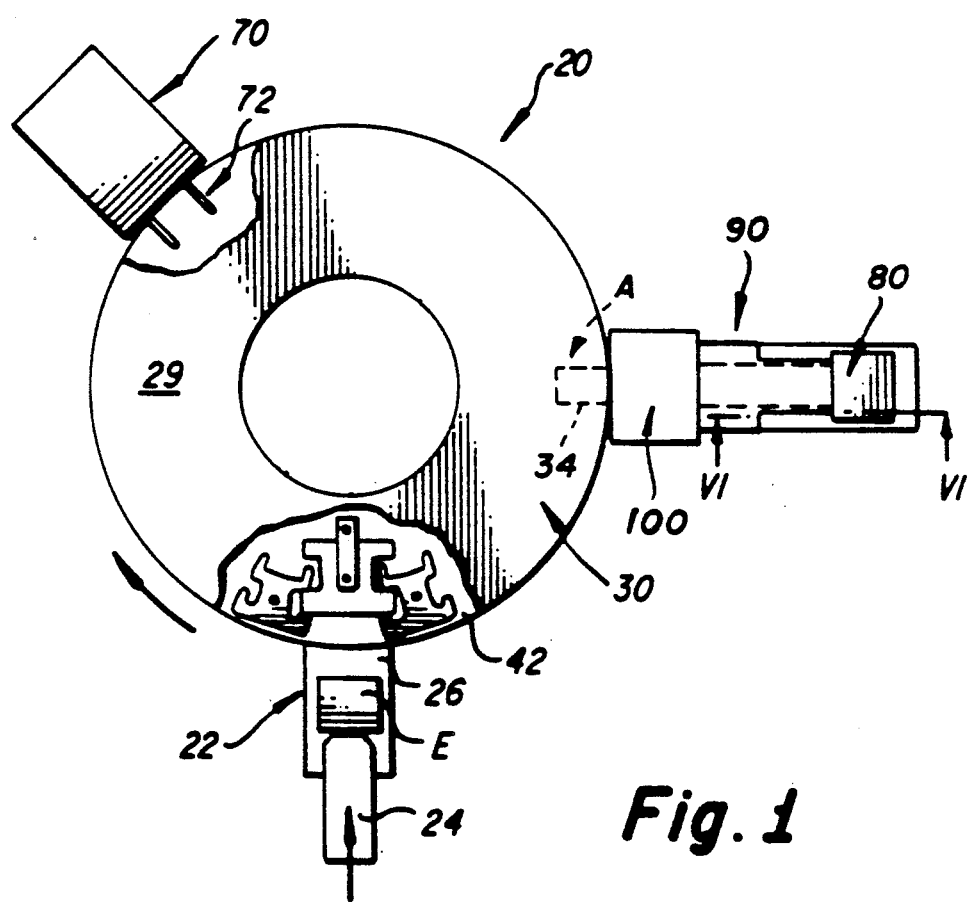
FIG. 1 is a partially broken away, partially schematic plan view of an analyzer constructed in accordance with the invention.

The invention is described hereinafter with respect to the preferred embodiment that is a complete analyzer that uses dried test elements, and particularly one that can be used in zero-G environments with a suitable incubator. In addition, it is useful in any device, analyzer or not, needing a transfer mechanism to move test elements through three or four stations, whether or not those stations include an incubator or process dried elements or liquid cuvettes, and whether or not gravity equals zero or something else.

Orientations such as "up", "down" or "vertical" refer to those as shown in the drawings, and are arbitrary if applied to use in a zero-G environment.

Referring to FIG. 1, an analyzer 20 constructed in accord with the invention comprises a sample-dispensing station 22, an incubator 30, means 24 for transferring test element E containing patient sample from station 22 into the incubator, a potentiometric read station 70 disposed adjacent to one side of incubator 30, a colorimetric read station 100 also disposed adjacent to the incubator and displaced circumferentially from read station 70, a container 80 to receive used test elements, and a guide 90 to direct such used test elements from read station 100 to container 80. Most preferably, transfer means 24 is a pusher blade activated and guided in a conventional manner by motors, etc., not shown, moved over a support surface such as surface 26.

Considering first the other parts of the analyzer, any suitable liquid dispensing means (not shown) is useful at station 22. Such station 22 can also include suitable structure (not shown) that restricts test element E to movement generally in contact with surface 26, particularly when used in a zero-G environment.

As is described in the commonly-owned application U.S. Ser. No. 293,718 filed by Hans Porte on 01/05/89 entitled "Incubator And Analyzer with Improved Cap Raising Means", incubator 30 features a stationary lower support plate 28, FIGS. 2 and 3, and a stationary upper cover plate 29. Either or both of these plates are heated in a conventional manner, with sensors, not shown, to provide feedback to control the incubator temperature as desired. Mounted between plates 28 and 29, FIGS. 2 and 3, is a rotor 32 providing individual test-element holding stations formed as pockets in the rotor. More specifically, indentations 34 are formed in rotor 32, as is also shown in FIG. 1, and hold-down leaf springs 35 are attached along the periphery of each indentation. The indentations are shaped and sized to hold a test element E therein, and springs 35 are shaped to press a test element against lower support plate 28, FIGS. 2 and 3. Preferably, springs 35 are dual springs that extend over the top of rotor 32, with a pair of fingers 36, 38 adjacent each indentation 34. Additionally, an evaporation cap 42 is provided, FIGS. 2 and 3, that is attached via a leaf spring 44 to rotor 32 to permit limited vertical movement, FIG. 3, arrow 46, of cap 42. Spring 44 is attached at 48 to rotor 32 and presses on cap 42. A rod 54 preferably rises out of cap 42, with a cam follower pin 56 that functions as described below.

To raise cap 42 when rotor 32 moves an indentation 34 adjacent plate 28 to a location to receive a test element, a cam 58 is provided, shown in phantom in FIG. 2. Cam 58 comprises a bridge element 62 fixed to the analyzer and a ramp 64, FIGS. 2 and 3. The shape of ramp 64 is constructed to cam pin 56 upward, and thus raise cap 42, as shown by arrow 66, FIG. 3.

Regarding potentiometric read station 70, FIG. 1, such station is conventional, and features a pair of electrodes 72 that raises and lowers into contact with appropriate parts of ion selective electrode (ISE) test elements held by rotor 32. That station is not activated until an ISE test element is positioned thereunder, ready for reading, as controlled by a suitable microprocessor, not shown. (Detection of which kind of test element is at which indentation 34 is done using a bar code reader at station 22, not shown.)

With respect to container 80, any suitable container can be used to collect used test elements. Preferably guide 90 is such as to keep such test elements constrained as they are pushed into the container, as described hereinafter, particularly if the analyzer is used in zero gravity environments.

Station 100 is the station that incorporates at least the colorimetric read station, and most importantly, it is the location of an important part of the transfer mechanism. In addition, part of that mechanism is present at station A, FIG. 1, in the incubator 30.

Figure 4:
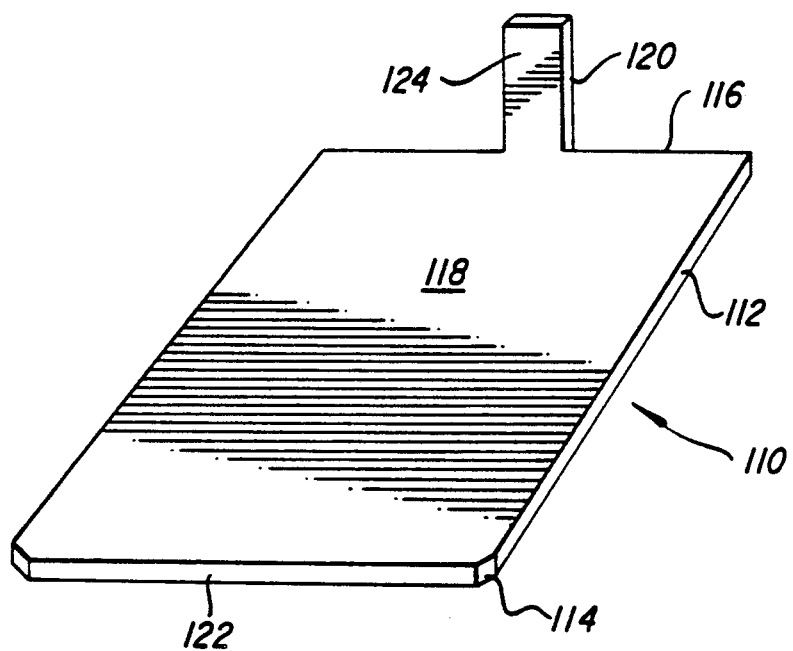
FIG. 4 is an isometric view of a preferred pusher blade used in the invention.

In accord with this invention, the transfer mechanism that moves a test element from the incubator station A, to two or three subsequent stations, such as read station 100, features a pusher blade 110 that is movably mounted for reciprocation below lower support plate 28, FIGS. 3-5. Such blade preferably comprises a flat body 112, FIG. 4, having a leading portion 114 at one end, a rear portion 116 at the opposite end, a test element support surface 118 between the leading and rear portions, and a pushing finger 120 rising vertically from rear portion 116. All these features form a simple integral piece with no moving parts. Leading portion 114 further includes a pushing surface 122, and the leading vertical surface 124 of finger 120 is also a pushing surface, as will become apparent.

Pusher blade 110, and its driving means integrally attached thereto, discussed below, comprise the only moving part(s) of this transfer mechanism. The rest of the transfer mechanism comprises, FIGS. 3 and 5A-5D, the lower support plate 28 of incubator 30, which provides a first support surface for test elements E at the location of station A, and a stationary lower support surface 130 on which pusher blade 110 rests and over which it reciprocates, as described hereinafter. Such surface 130 provides additional test element locations at station C and D.

Reciprocation of pusher blade 110 is preferably provided by an ear 132 extending below body 112, to which is attached a driver such as a piston rod 134, FIGS. 3 and 5A-5D. That rod in turn is connected to moving means such as a piston cylinder 136, FIGS. 5A-5D. Alternatively, any other suitable driving mechanism can be used in place of the hydraulic rod 134 and piston 136.

Because pusher blade 110 includes two portions that extend out of the plane of body 112, that is, finger 120 and ear 132, an appropriate slot 140 and groove 150 are formed in lower support plate 28 of incubator 30, and in support surface 130. An additional groove 152 is preferably provided in rotor 32 to allow finger 120 to remain within the incubator while rotor 32 rotates above it, FIGS. 5A and 5C.

Figures 5A, 5B:
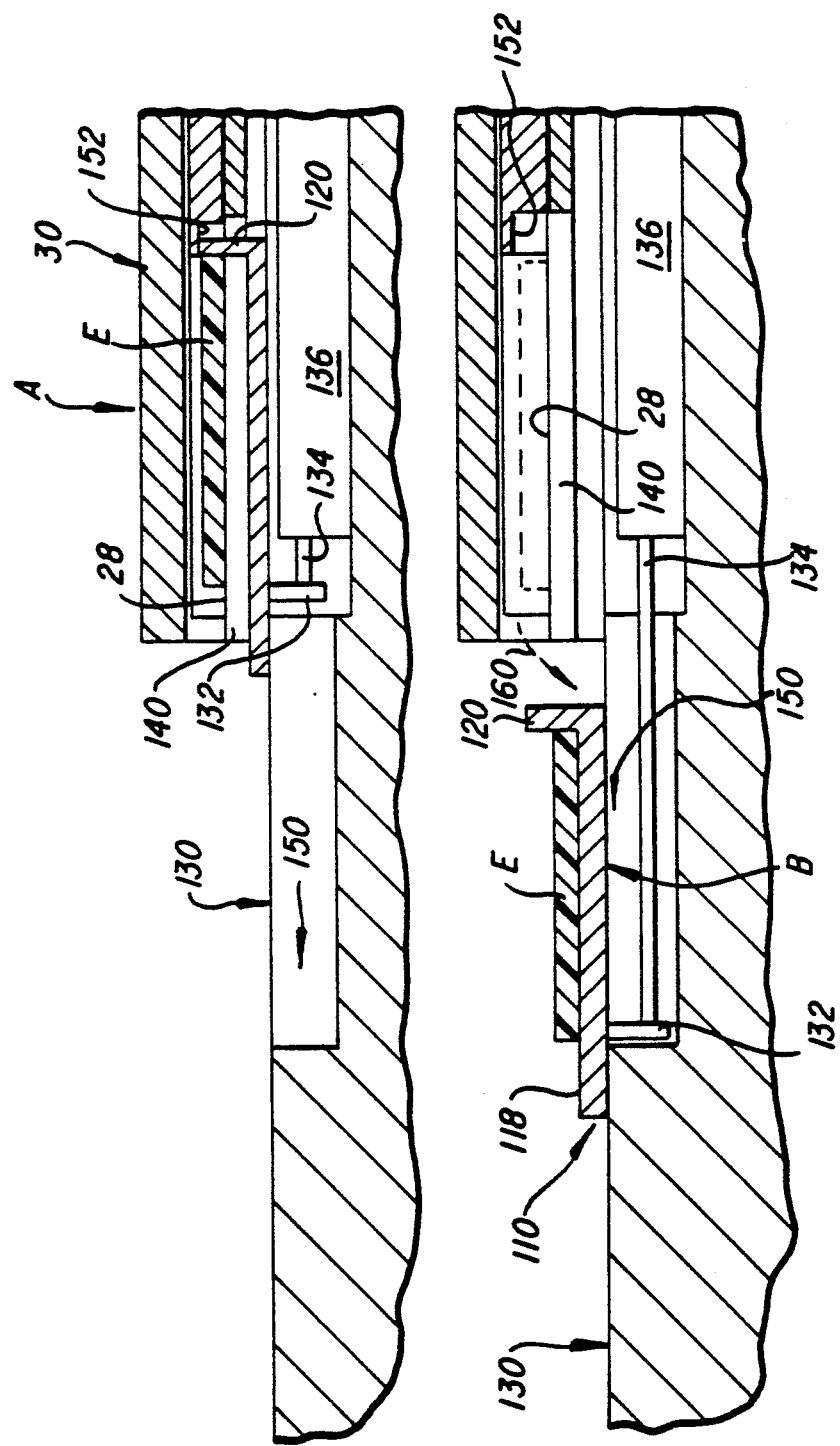

The use of this transfer mechanism will be apparent from the above description. Referring particularly to FIGS. 5A–5D, the process is as follows:

The first of the three or four test element locations involved in the transfer is the location at station A, inside incubator 30, FIG. 5A, when the test element rests on the surface of plate 28. At this location, finger 120 is behind element E, so that when moving means 134 and 136 are activated, finger 120 and blade 110 move out from underneath support plate 28, pushing test element E off (arrow 160) the surface of plate 28 and onto support surface 118 at station B, FIG. 5B.

Next, blade 110 is retracted back to its position underneath support plate 28, FIG. 5C. Because at this point the undersurface of plate 28 is spaced just above surface 118 of blade 110, FIG. 3, to provide room only to allow blade 110 to retract and not also test element E, that element is pushed off of blade 110, arrow 170, FIG. 5C, onto support surface 130, at station C. Station C is different from station B in that it is at least at a level below station B. In addition, as shown, it is moved closer to incubator 30 since it is the outer edge 172 of the lower incubator support plate 28 that pushes off the test element. (Alternatively, not shown, additional structure can be provided to push off the test element before it is retracted to a position adjacent the incubator, so that station C is directly below station B, if desired.) While the test element is at station C, additional processing is optionally done on the test element, for example, washing with a wash liquid from a pipette "P". Also while element E is at station C, rotor 32 of incubator 30 is preferably further advanced so as to bring a second test element E' into station A.

Optionally, and preferably if the invention is used in zero-G environments, a fixed member (not shown) is positioned just above station B, FIG. 5B, to keep elements at station B from moving away from surface 118. Such a member is also effective in aiding the retention of elements at station C from unwanted movement away from surface 130. For example, a leaf spring (not shown) can be mounted to apply a force F, FIG. 5B, on element E as it comes out of station A, to force it down onto blade 110 or surface 130, FIG. 5C.

Thereafter, when pusher blade 110 is moved out from under support 28, FIG. 5D, it acts to do two things: it pushes element E' off support plate 28 and onto its surface 118, as occurred previously with element E. In addition, and simultaneously, blade 110 acts to move element E from station C (FIG. 5C) to station D. The latter occurs by reason of pushing surface 122 pushing element E forward.

Station D can be any subsequent processing station. Most preferably, it is the read station 100 for elements E and E', and therefore comprises a light source 180 of conventional construction, and an aperture 182 allowing a beam 184 to scan element E. Reflected light is collected at an angle different from the angle of beam 184 and sent via lenses to a photodetector (not shown). Optionally, a cover 186 is brought down (arrow 188) onto element E at station D.

Depending on the length of blade 110, an element E that has been read at station D, can be moved onto guide means 90 by reason of the next element E' pushing it out of station D, when that element E' is advanced to station D, as shown; or that element E can be moved out by the blade itself if it is long enough (not shown).

The invention has been described in detail with particular reference to preferred embodiments thereof, but it will be understood that variations and modifications can be effected within the spirit and scope of the invention.

What is claimed is:

1. A transfer mechanism for moving a test element from a first location in a clinical analyzer to a second location in a clinical analyzer disposed at a different level than said first location, comprising
a first support surface defining the first location,
a pusher blade positioned under said first support surface and having a leading portion, a rear portion, and a flat support surface thereon extending the entire distance between said leading portion and said rear portion, for receiving and supporting a test element in the second location, said pusher blade further including an upwardly extending finger portion integrally formed with and extending from said rear portion, said first support surface having a slot formed therein to accommodate said finger portion, and
moving means for moving said blade from the first location in which it is directly under said first support surface to the second location at which said blade is no longer under said first support surface so that the first and second locations are at different vertical levels.

2. A transfer mechanism as defined in claim 1 further including a fixed lower support surface under said pusher blade on which said moving means moves said blade, said lower support surface defining a third location disposed at a different level than either the first or second locations.

3. A transfer mechanism as defined in claim 2, wherein said blade is mounted for reciprocating movement immediately above said lower support surface.

4. A transfer mechanism as defined in claim 2 or 3, wherein said pusher blade has a pushing surface formed at said leading portion for moving a test element from the third location to a fourth location on said lower support surface.

5. A transfer mechanism as defined in claims 2 or 3, wherein said means for moving said pusher blade comprises a hydraulic piston and a dependent ear portion on said blade to which said piston is connected, said ear portion moving in a groove formed in said support surface.

6. A transfer mechanism as defined in any one of claims 1–3, wherein said slot extends generally through the middle of said first support surface in a direction in which a test element is to move relative to said support surface.

7. A biological liquid analyzer comprising incubating means for incubating a test element containing a sample of patient liquid thereon, said incubating means including a first support surface which defines a first location, processing means for processing an incubated test element, and a transfer mechanism for moving an incubated test element from the first location to said processing means, said transfer mechanism comprising a pusher blade positioned under said first support surface and having a leading portion, a rear portion, and a flat support surface thereon extending the entire distance between said leading portion and said rear portion, for receiving and supporting a test element in the second location, said pusher blade further including an upwardly extending finger portion integrally formed with and extending from said rear portion, said first support surface having a slot formed therein to accommodate said finger portion, and moving means for moving said blade from the first location in which it is directly under said first support surface to the second location at which said blade is no longer under said first support surface so that the first and second locations are at different vertical levels.

8. An analyzer according to claim 7, wherein said processing means includes a read station for measuring a change in an incubated test element.

9. A method of moving a test element through more than two separate locations using a single moving element having an upwardly projecting portion at one edge, the first of said locations being located on a first support surface and said moving element being movably located under said support surface with means to guide it out from underneath said support surface with a clearance less than the thickness of a test element, the method comprising the steps of a) disposing a test element into said first location on said support surface;

b) positioning said moving element while underneath said support surface so that said projecting portion of the moving element projects through the support into contact with a rear edge of a test element;

c) moving said moving element on a single level completely out from underneath said support surface until said projecting portion pushes the contacted test element off said support surface into a second location on said moving element; and d) retracting said moving element underneath said support surface until said support surface pushes a test element carried by said moving element, off of it into a third location on a second support surface in front of said moving element.

10. A method as defined in claim 9, and further including the step of:

e) repeating the movement of said moving element recited in step c) so as to push via the leading edge of said moving element, a test element from said third location to a fourth location.

* * * * *